(12) United States Patent
Altaffer et al.

(10) Patent No.: US 7,048,941 B2
(45) Date of Patent: May 23, 2006

(54) CHOCOLATE COMPOSITION AS DELIVERY SYSTEM FOR NUTRIENTS AND MEDICATIONS

(75) Inventors: Paul Altaffer, San Francisco, CA (US); Alexander R. Conn, Austin, TX (US); Joshua A. Duberman, Bellevue, WA (US); David Lytle, Sandy, OR (US); Kerry Hughes, San Rafael, CA (US)

(73) Assignee: New World Enterprizes, Inc., San Leandro, CA (US)

( * ) Notice: Subject to any disclaimer, the term of this patent is extended or adjusted under 35 U.S.C. 154(b) by 249 days.

(21) Appl. No.: 10/107,664

(22) Filed: Mar. 26, 2002

(65) Prior Publication Data

US 2002/0192316 A1 Dec. 19, 2002

Related U.S. Application Data

(60) Provisional application No. 60/279,716, filed on Mar. 30, 2001.

(51) Int. Cl.
*A61K 47/00* (2006.01)
*A61K 35/78* (2006.01)

(52) U.S. Cl. ................. 424/439; 424/725; 424/776
(58) Field of Classification Search ............... 424/439, 424/435, 725, 776
See application file for complete search history.

(56) References Cited

U.S. PATENT DOCUMENTS

| | | | |
|---|---|---|---|
| 4,246,256 A | 1/1981 | Lembke et al. | |
| 4,271,142 A | 6/1981 | Puglia et al. | |
| 4,749,575 A | 6/1988 | Rotman | |
| 4,818,539 A | 4/1989 | Shaw et al. | |
| 5,198,230 A | 3/1993 | Wen | |
| 5,504,105 A | 4/1996 | Chiesi et al. | |
| 5,525,352 A | 6/1996 | Kontos et al. | |
| 5,554,645 A | 9/1996 | Romanczyk, Jr. et al. | |
| 5,560,955 A | 10/1996 | Izzo et al. | |
| H1620 H | 12/1996 | Dolan et al. | |
| 5,612,074 A | 3/1997 | Leach | |
| 5,674,522 A | 10/1997 | Shah et al. | |
| 5,712,305 A | 1/1998 | Romanczyk, Jr. et al. | |
| 5,756,467 A | 5/1998 | Kagawa et al. | |
| 5,853,747 A | 12/1998 | Ponroy | |
| 5,877,206 A | 3/1999 | Romanczyk, Jr. et al. | |
| 5,891,905 A | 4/1999 | Romanczyk, Jr. et al. | |
| 6,015,913 A | 1/2000 | Kealey et al. | |
| 6,051,236 A | 4/2000 | Portman | |
| 6,133,311 A | 10/2000 | Bok et al. | |
| 6,156,791 A | 12/2000 | Romanczyk, Jr. et al. | |
| 6,156,912 A | 12/2000 | Tuckmantel et al. | |
| 6,174,542 B1 | 1/2001 | Hinton et al. | |
| 6,194,020 B1 | 2/2001 | Myers et al. | |
| 2001/0008641 A1 | 7/2001 | Krotzer | |
| 2002/0172732 A1* | 11/2002 | Ter Laak et al. ........... | 424/776 |

FOREIGN PATENT DOCUMENTS

| | | |
|---|---|---|
| WO | WO 98/02165 | 1/1998 |
| WO | WO 99/45797 | 9/1999 |
| WO | WO 99/61038 | * 12/1999 |
| WO | WO 02/38141 A | 5/2002 |

OTHER PUBLICATIONS

"Chocolate: Food or Drug" in Ingredients for Health, Kerry Hughes, edited, Sep. 2000.*

Chcolate: Food or Drug? By Bruinsma et al. in the American Dietetic Association. The Journal Of the American Dietetic Association. Chicago: Oct. 1999, vol. 99, Issue 10; pp. 1249-1256.*

Ian Knight, Ed., Chocolate and Cocoa: Health and Nutrition, 1999, pp. 3-8, 63-75, 89-115, 143-173, 177-194, 240-278, 310-338, Blackwell Science Ltd., Oxford.

Teresa L. Dillinger, Patricia Barriga, Sylvia Escarcega, Martha Jimenez, Diana Salazar Lowe, and Louis E. Grivetti, Food of the Gods: Cure for Humanity? A Cultural History of the Medicinal and Ritual Use of Chocolate, presented at the symposium "Chocolate: Modern Science Investigates as Ancient Medicine," held Feb. 19, 2000, 2000 Annual Meeting and Science Innovation Exposition at the American Association for the Advancement of Science in Washington, D.C.

(Continued)

*Primary Examiner*—Michael Hartley
*Assistant Examiner*—Blessing Fubara
(74) *Attorney, Agent, or Firm*—Donald R. Boys; Central Coast Patent Agency, Inc.

(57) ABSTRACT

A novel chocolate product for use in delivering medicaments and/or nutrients to animals, particularly humans, specially formulated so that the craving for such product by animals, particularly humans, is significantly greater than the craving for chocolate conventionally used in pharmaceutical compositions and the concentration, optimization, and the addition of endogenous and exogenous ingredients to increase such craving as well as to treat specific indications. The chocolate product contains: from about 0.5 to about 200 milligrams, more preferably from about 5 to about 20 milligrams, of one or more biogenic amines per 1 gram of the chocolate product; from about 10 to about 500 milligrams, more preferably form about 20 to about 200 milligrams, of one or more amino acids per 1 gram of the chocolate product; (C) from about 1 microgram to about 20 milligrams, more preferably from about 10 micrograms to about 10 milligrams, of one or more of: methyl tetrahydroisoquinoline, N-acylethanolamines, and/or anandamide and/or salsolinol per 1 gram of the chocolate product; (D) from about 0.2 to about 30 milligrams of at least one trace mineral per 1 gram of the chocolate product; and (E) from 0.6 to about 500 milligrams, more preferably from about 35 to about 100 milligrams, of one or more methylxanthine alkaloids per 1 gram of the chocolate product. The chocolate product used in this invention also preferably contains effective amounts of at least one chocolate aroma and at least one vanilla aroma.

38 Claims, No Drawings

OTHER PUBLICATIONS

Kristen Bruinsma, M.S. and Douglas L. Taren, Ph.D, Chocolate: Food or drug?, Journal of the American Dietetic Association, Oct. 1999, pp. 1249-1255, vol. 99, No. 10.

Kerry Hughes, Chocolate: Food or Drug?, Sep. 2000, www.Preparedfoods.com.

Jean Carper, Sweet news about chocolate, Issue date: Jun. 5-7, 1998, USA Weedkend (Archive) on-line, Eat Smart, www.usaweekend.com/98.

S. Rossner, Chocolate—divine food, fattening junk or nutritious supplementation? Recieved Nov. 10, 1996, Stockton Press, pp. 341-345.

J.C. Melchior, D. Rigaud, N. Colas-Linhart, A. Petiet, A. Girard and M. Apfelbaum, Immunoreactive Beta-Endorphin Increases After an Aspartame Chocolate Drink in Healthy Human Subjects, Physiology & Behavior, 1991, pp. 941-944, vol. 50, Pergamon Press, US.

No Author, Psychoactive Food and the Chocolate Amphetamine, May 2002, www.chocolate.org.

Willa Michener and Paul Rozin, Pharmacological Versus Sensory Factors in the Satiation of Chocolate Craving, Physiology & Behavior, 1994, pp. 419-422, vol. 56, No. 3, Elsevier Science Ltd., US.

Jennie I. Macdiarmid and Marion M. Hetherington, Mood modulation by food: an exploration of affect and cravings in 'chocolate addicts,' British Journal of Clinical Psychology, 1995, pp. 129-138, vol. 34, Great Britain.

Regina Tomelleri, M.S. and Katharine K. Grunewald, PH.D., R.D., Menstrual cycle and food cravings in young college women, Journal of the American Dietetic Association, Mar. 1987, pp. 311-314, vol. 87, No. 3, US.

Majorie Schuman, PH.D., Michael J. Gitlin, M.D., and Lynn Fairbanks, PH.D., Sweets, Chocolate, and Atypical Depressive Traits, The Journal of Nervous and Mental Disease, 1987, pp. 491-495, vol. 175, No. 8, US.

W. Jeffery Hurst, Robert A. Martin, Jr., PH.D., Barry L. Zoumas, PH.D. and S.M. Tarka, Jr., Biogenic Amines in Chocolate—A Review, Nutrition Reports International, Dec. 1982, pp. 1081-1085, vol. 26, No. 6.

W. Jeffrey Hurst and Paul B. Toomey, High-performance liquid chromatographic determination of four biogenic amines in chocolate, Analyst, Apr. 1981, pp. 394-402, vol. 106.

A.J. Greenshaw, β-Phenylethylamine and reinforcement, Prog. Neuro-Psychopharmacol & Biol Psychiatry, 1984, pp. 615-620, vol. 8, Psychiatric Research Division, Saskatchewan Health, University of Saskatchewan, Saskatoon, Saskatchewan, Canada.

Jack W. Schweitzer, Arnold J. Friedhoff, and Ralph Schwartz, Chocolate, β-phenethylamine and migraine re-examined, Nature, Sep. 18, 1975, p. 256, vol. 257.

A. Marcus, L. Scharff, D. Turk, L.M. Gourley, A double-blind provocative study of chocolate as a trigger of headache, Cephalalgia, 1997, pp. 855-862, vol. 17.

K.A. Hosteler, R.B. Morrissey, S.M. Tarka, Jr., J.L. Apgar and C.A. Shively, Three-generation reproductive study of cocoa powder in rats, Ed. Chem. Toxic., 1990, pp. 483-490, vol. 28, No. 7, Pergamon Press, Great Britain.

A.G. Dulloo, J. Seydoux, and L. Girardier, Potentiation of the thermogenic antiobesity effects of ephedrine by dietary methylxanthines: adenosine antagonism or phosphodiesterase inhibition?, Metabolism, Nov. 1992, pp. 1233-1241, vol. 41, No. 11.

S.R. Philips and A.M. Robson, In vivo release of endogenous dopamine from rat caudate nucleus by phenylethylamine, Neuropharmacology, 1983, pp. 1297-1301, vol. 22, No. 11, Great Britain.

Charlea T. Massion, MD, Chocolate: Food, Drug, or Lifestyle?, Alternative Therapies in Women's Health, Dec. 2001, pp. 89-93, vol. 3, No. 12.

* cited by examiner

CHOCOLATE COMPOSITION AS DELIVERY SYSTEM FOR NUTRIENTS AND MEDICATIONS

CROSS-REFERENCE TO RELATED DOCUMENTS

The present non-provisional patent application claims priority to provisional application Ser. No. 60/279,716 Mar. 30, 2001, which is incorporated herein in its entirety by reference.

FIELD OF THE INVENTION

The present invention is in the field of carriers for administering nutrient and/or medicant compositions to animals, particularly to humans, and pertains more particularly to the preparation of such carriers to enhance the probability of consistent use by the animals for which the carrier is intended.

BACKGROUND OF THE INVENTION

This invention relates to carriers for use in nutrient- and/or medicament-containing compositions designed to treat various ailments health conditions that commonly occur in mammals. More particularly, this invention relates to a novel chocolate composition as a delivery system for nutrients and medications wherein the composition is formulated to increase a patient's desire to consume the nutrients and medications delivered by the composition. In addition, this invention relates to a novel chocolate composition which itself constitutes an effective nutritional product.

Treatments are available today for a wide variety of ailments which afflict humans, e.g., obesity, depression, sexual dysfunction, premenstrual stress syndrome, etc. However, despite the fact that available treatments may have been proven safe and effective by studies of the highest scientific standards, most treatments fail and most ailments seem to defy eradication. Humans still suffer from both age-old diseases such as sexual dysfunction and women's health problems, or more modern diseases such as obesity or depression. (see: Garrett, Laurie, 1995; Diamond, Jared, 1997; 1999). The cost of conventional treatments can be considerable, it is estimated that for the treatment of osteoarthritis, treatment with NSAIDS(non-steroidal anti-inflammatory drugs) costs up to $90/month; for congestive heart failure the cost of treatment is $200,000–400,000; for benign prostatic hypertrophy $5,000 for Proscar (the most common drug prescribed); and for elevated cholesterol it is estimated to cost $30–125/month. These costs are considerable, especially when it is realized that many of these illnesses could be prevented or mitigated if they were managed at earlier stages (Price, 1995). Furthermore, most people in developing countries, or poor parts of developed countries can simply not afford such treatments. Failure to get treatments can overburden the public health system costing many hundreds of balm of dollars annually! (see: WHO reports; United States Center for Health Statistics Annual Reports and National Institute for Health Reports).

A significant cause of such treatment failure is that compliance by patients in taking their medicine is inconsistent at best. Oral ingestion is the most common way in which medications or nutrients are consumed. However, many people consider oral forms of medications or nutrients to be unpalatable. Some people also consider orally administered medications or nutrients to be invasively risky because of the presence of synthetic compounds therein. Surprisingly, many patients will not consistently take their medication even when their lives are at risk and the treatment is simple (see: Garrett, Laurie, 1995; pages 440 . . . ). Even "one-a-day" vitamins are often not taken daily. As a result, compliance with, and, therefore, the effectiveness of, oral treatments vary from patient to patient.

Thus, in spite of the effectiveness, safety and convenience of many modern treatments for a variety of ailments, such treatments often fail because people do not properly follow their prescriptions or regularly eat their supplements (see Garrett, Laurie, 1995).

Many attempts to overcome patient non-compliance with oral treatments have involved altering the route of administration and/or the dosage. However, simply changing the route of administration or making stronger dosages has only marginally improved patient compliance.

Efforts to improve patient compliance have also involved modifying or fortifying conventional foods to create "medicinal foods". For example, such efforts have included increasing the levels of endogenously occurring ingredients in already-nutritional foods (e.g., fortifying orange juice with additional vitamin C) or adding nutritional or medicinal ingredients to foods which have limited or no nutritional or medicinal value (e.g., adding vitamins to breakfast cereal). However, these efforts do not really address the problem of patient non-compliance or variability. For example, just because a person perceives orange juice to be healthy does not mean that he will drink it, even if he has a cold. Simply fortifying the juice with vitamin C will not increase the non-compliant patient's motivation to drink it.

It is desirable, therefore, to provide a composition for delivering nutrients and/or medicines to humans which is more effective than prior art compositions in increasing patient compliance with oral treatments. It is particularly desirable that such composition contain mostly natural ingredients.

In contrast to their reaction to fortified or purified foods of the type discussed above, most people will eagerly ingest foods which they crave. In fact, people will ingest craved foods even if they understand such foods to be unhealthy or harmful to them.

One particularly craved food is chocolate.

The use of chocolate in pharmaceutical compositions is known in the art. Examples of references teaching such use of chocolate are discussed below.

WO 98/02165 (international filing date: Jul. 16,1997; international publication date: Jan. 22,1998) discloses a method and composition for reducing appetite and carbohydrate craving using precursors for the neurotransmitters serotonin, dopamine, norepinephrine, and histamine, which include the precursors tryptophan, phenylalanine, tyrosine and histidine. According to the reference, the precursors are combined together and with xanthines for synergistic effect permitting advantageously lower doses of the precursors. Xanthines, including theobromine, caffeine and cocoa, act as potentiators of the precursors. The reference teaches that the xanthines may be derived from natural sources used in foodstuffs, such as cocoa, tea, coffee and the like.

WO 99/61038 (international filing date: May 28,1999; international publication date: Dec. 2, 1999) discloses a composition containing a nutritionally beneficial substituent and a substituent that provides psychological feedback. Specific examples of the latter substituent include caffeine, tryptophan, cocoa, and chocolate.

U.S. Pat. No. 6,174,542 (Hinton, et al.) discloses dietary supplements and food products for treating symptoms of PMS, wherein the supplements and food products contain chocolate, vitamins, herbs and minerals. According to the patent, the primary object of the invention therein was to provide a dietary snack food product that satisfies a PMS sufferer's craving for foods high in fat and sugar, such as chocolate, while delivering herbs, vitamins and minerals that can help alleviate, treat, prevent and manage symptoms associated with PMS. Examples of suitable snack foods include granola bars, chocolate bars, cookies, chocolate brownies, chocolate cakes, ice cream and yogurt. Examples of suitable chocolates include white, dark, milk, carob, sweetened and semi-sweetened. Alternatively, according to the patent, ingredients and components derived from chocolate can be used to enhance, or even be substituted for, the chocolate.

U.S. Pat. No. 4,749,575 (Rotman) discloses an orally administrable medicament which, according to the patent, eliminates the unpleasant taste and mouth feel of the medicament and is easily and pleasantly ingested, wherein the medicament is microencapsulated into microcapsules of less than 300 microns diameter, and the microcapsules are then embedded into a soft, sweet, palatable matrix, such as chocolate.

U.S. Pat. No. 5,853,747 (Ponroy) discloses a phospholipid-based preparation for use in treating aging disorders, wherein the preparation contains purified pig brain phospholipids alone or in combination with a carrier for oral delivery. Examples of such carriers include cereal flours, fats, inert carriers, carriers and milk derivatives.

U.S. Pat. No. 6,051,236 (Portman) discloses a nutritional composition for optimizing muscle performance during exercise and for enhancing muscle cell repair and recovery following the cessation of exercise, wherein the composition includes a carrier that can be in the form of chocolate, oats, wheat, peanut butter, semi-dried fruits, grains and combinations therein for providing a semi-liquid carrier to the dry powder of the nutritional composition.

U.S. Pat. No. 5,525,352 (Kontos, et al.) discloses a confectionery delivery system for controlled release of pharmaceutically active substances, wherein the delivery system is composed of coated microcapsules containing a pharmaceutically active substance and surrounded by a confectionary matrix. The confectionary matrix is preferably ice cream, and the microcapsules may be coated with chocolate. The delivery system is soluble in the mouth and readily swallowed without chewing.

U.S. Pat. No. 5,674,522 (Shah, et al.) discloses a beverage concentrate for delivering orally administrable pharmaceutical actives; wherein the beverage concentrate contains an instant food, the pharmaceutical active, and sweetening and flavoring agents. According to the patent, the instant food is one which will form a pleasant tasting, hot liquid beverage when added to hot water. Suitable instant foods include instant tea, instant coffee, instant soup and instant cocoa.

U.S. Pat. No. 5,198,230 (Wen) discloses a composition for curing drug addiction, wherein the composition can be combined with cocoa powder to form a chocolate candy.

U.S. Pat. No. 5,560,955 (Izzo, et al.) discloses a protein composition having reduced hygroscopic properties, wherein the composition may be incorporated into an edible carrier such as, e.g., chocolate.

U.S. Pat. No. 4,271,142 (Puglia, et al.) discloses a portable liquid antacid in the form of an antacid tablet including a center portion containing an antacid in the form of a liquid, cream or gel and, optionally, a chocolate flavorant, encased in or surrounded by a fat-containing coating, such as a chocolate coating.

U.S. Pat. No. 4,246,256 (Lembke et al.) discloses an edible or oral composition which limit the development of tooth decay, wherein the composition can be in the form of a milk chocolate bar containing cocoa paste, sucrose, milk fat and lactate dehydrogenase in an amount sufficient to limit the promotion of tooth decay.

U.S. Pat. No. 5,504,105 (Chiesi, et al.) discloses an orally administrable pharmaceutical composition having antiosteoporotic and antihypercalcemic properties containing ipriflavone as the principal active ingredient together with a vehicle selected from the group consisting of hydrogenated vegetable oils, glycerides, white chocolate, soya lecithin, and mixtures thereof.

U.S. Pat. No. 5,756,467 (Kagawa, et al.) discloses a food composition for inhibiting adipocyte differentiation composed of an effective amount of an adipocyte differentiation inhibiting peptide and a food, wherein the food can be, e.g., chocolate, milk, pudding, curry, hash, stew, meat sauce, ham or cake. According to the patent, the invention therein prevents and treats obesity and cardiovascular diseases.

U.S. Pat. No. 6,133,311 (Bok, et al.) discloses a method for preventing or treating elevated blood lipid level-related diseases by administering natural phenolic compounds which can be in the form of a food composition. Examples of such food compositions include, e.g., chocolate, meat, pizza, confectionery, etc.

U.S. Pat. No. 4,818,539 (Shaw, et al.) discloses a delivery system comprising an edible matrix and an ingestible substantially anhydrous aggregate consisting essentially of a pre-swelled hydrocolloid and a substate. The edible matrix can be composed of hydrogenated vegetable oil, chocolate and cocoa butter.

SIR No. H1620 Polan, et al.) discloses a dry chocolate-flavored beverage mix composed of cocoa powder, sugar, caramel powder, malt extract, flavor enhancing salt, powdered non-dairy creamer, a thickening agent, added lecithin, an antioxidant, and nutritionally supplemental amounts of vitamins and minerals.

U.S. Pat. No. 5,612,074 (Leach) discloses a nutrient fortified food bar containing various ingredients including vitamins, magnesium, amino acids, etc., wherein the food bar may be coated with such materials as while chocolate, peanut, caramel, honey, carob, fruit and yogurt.

U.S. Pat. No. 6,015,913 (Kealey et al.) discloses a method of processing a fat-containing bean, e.g., cocoa beans, for producing solids containing active polyphenols and/or fat-containing products, comprising extracting the fat to produce solids and fat-containing solids. According to the patent, the method provides cocoa compositions containing at least active polyphenol, wherein the concentration of the polyphenol(s) relative to the nonfat solids is conserved with respect to the concentration of the active polyphenol(s) in the bean from which the compositions are derived.

WO 99/45797 discloses foods and pharmaceuticals which contain cocoa and/or nut procyanidins in combination with L-arginine, wherein the foods and pharmaceuticals are said to be effective in inducing a physiological increase in nitric oxide production.

U.S. Pat. No. 6,194,020 (Myers, et al.) discloses food products, including confectioneries and chocolates, having conserved concentrations of polyphenols, and, in particular, cocoa polyphenols.

U.S. Pat. Nos. 5,877,206; 5,891,905; 5,712,305; 5,554,645; and 6,156,791 (all to Romanczyk, Jr. et al.) disclose antineoplastic compositions containing cocoa polyphenols or procyanidins.

However, the above-described references which discuss the use of chocolate for nutritional or medicinal purposes deal with simple purification or fortification of specific constituents. Constituents in chocolate are isolated, extracted or in some way purified. The intent is to reduce or avoid the supposedly unhealthy aspects of chocolate by emphasizing the specific constituents (see, e.g., the Myers, et al. Romanczyk, Jr. et al. patents discussed above, as well as U.S. Pat. No. 6,156,912 to Tuckmantel et al.).

None of the above-cited references teaches the use of chocolate in pharmaceutical compositions because of chocolate's property of being craved by patients. Instead, the references completely and mistakenly overlook the unique and surprising value of chocolate as the food that is the most craved by humans. Furthermore, one skilled in the art would be confused by the great contradictions in the prior art regarding the efficacy and mechanisms behind chocolate craving (see: Donohoe, R T, 1999; AHFS no. 28.16.04; The Tallahassee Democrat, Sep. 1, 1995).

Chocolate is perceived and consumed today as a hedonistic confection, not for health purposes. However, this has not always been the case. The medicinal use of chocolate, both as a primary remedy and as a vehicle to deliver other medicines, originated in the New World with the Olmec, Maya and Aztec Indians and diffused to Europe in the mid 1500s. Early colonial era accounts document medicinal uses that included treatment of: fatigue, fever, panting of breath and to treat the faint of heart. Subsequent 16th to early 20th century European manuscripts revealed well over 100 medicinal uses for chocolate.

As a therapeutic agent, chocolate has been used to: 1) to treat emaciated patients to gain weight; 2) to stimulate nervous systems of apathetic, exhausted or feeble patients; and 3) to improve digestion and elimination where chocolate countered the effects of stagnant or weak stomachs, stimulated kidneys and improved bowel function. Chocolate has also been used to treat anemia, poor appetite, mental fatigue, poor breast milk production, consumption/tuberculosis, fever, gout, reduced longevity and poor sexual appetite/low virility. Lastly, as the patents listed hereinabove teach, chocolate paste has been used as a medium for administering drugs and for countering the taste of bitter pharmacological additives.

Chocolate is craved across all demographic groups. The reasons for this craving are not merely cultural or psychological but also physiological. The primary physiological mechanisms involved with chocolate cravings are sensory associations (including chocolate's unique taste, smell and color) and neurochemical or nutritional "feeding" (including chocolate's high content of key neurochemical precursors, vitamins, minerals and other ingredients).

The endogenous ingredients responsible for the physiological activity of chocolate and the craving for chocolate include the following groups: methylxanthine alkaloids, biogenic amino acids, trace minerals, and "cannibinol-like compounds", this latter group of ingredients belonging to several classes of chemicals. In addition, aromatics and pigment contribute to chocolate's unique taste, smell and color.

The present inventors have found that, in its natural confectionery form, chocolate does not contain sufficient amounts or the optimum ratios of the ingredients identified as being responsible for chocolate's physiological craving to assure that chocolate will work as an efficient nutritional or medical delivery system. Nor will chocolate in its natural state contain sufficient amounts or the optimum ratios of the ingredients needed to treat specific indications. Because the amounts and proportions of the ingredients responsible for chocolate's physiological craving, or the ingredients needed to treat specific indications, are inadequate in chocolate's natural confectionery form, ingestion of large quantities of chocolate would be necessary for the chocolate to function effectively as a delivery system for nutrients and/or medicaments.

The present inventors have also found that the fortified forms of chocolate identified in the prior art also do not contain sufficient amounts and/or the optimum ratios of the ingredients responsible for craving, or the ingredients needed to treat specific indications, to work as a nutritional or medical delivery system.

Since chocolate is expected to be a confection, large amounts of sugar and fat are typically added to it, or large amounts of saturated fat is left in. Thus, ingestion of large quantities of chocolate in its natural confectionery form would include unwanted ingredients which are deleterious to health.

A primary objective of this invention is to provide a composition for delivering nutrients and/or medicaments to animals, preferably humans, wherein the composition has a formulation which the animal will readily orally ingest.

A further object of this invention is to provide a composition for delivering nutrients and/or medicaments to animals, preferably humans, wherein the composition is one which is craved by the animal such that the animal will readily orally ingest the composition.

Another object of this invention is to provide a composition having the features described in the preceding objects, wherein the composition is substantially composed of natural ingredients.

Yet another object of this invention is to provide a composition for delivering nutrients and/or medicaments to animals, preferably humans, wherein the composition is composed of a novel chocolate product the craving for which by animals, particularly humans, is greater than the craving for conventional chocolate substances used in pharmaceutical compositions.

Still yet another object of this invention is to provide a composition for delivering nutrients and/or medicaments to animals, preferably humans, wherein the composition is composed of a novel chocolate product that contains the ingredients to treat specific indications, wherein the ingredients may be endogenously occurring in chocolate and have been concentrated and/or optimized or exogenously added to the chocolate composition.

These and other objects are achieved in the present invention, as described hereinbelow.

SUMMARY OF THE INVENTION

The present invention provides a novel chocolate product for use in delivering medicaments and/or nutrients to animals, particularly humans. The chocolate product of this invention is specially formulated so that the craving for such product by animals, particularly humans, is significantly greater than the craving for chocolate conventionally used in pharmaceutical compositions.

The present invention is based in part on the discovery that for a chocolate-containing delivery system or carrier to have more than just the normal craving casually associated with chocolate or a simple placebo effect, or, not to counteract the intended treatment, the ingredients responsible for the physiological cravings must be present in at least minimum amounts and in the correct proportions. If a delivery system does not contain sufficient amounts or ratios of the ingredients responsible for the physiological craving for chocolate, the chocolate will counteract the benefits of the nutritional or medical delivery system and possibly worsen the specific indications intended to be treated.

The present invention concentrates and optimizes those ingredients that are responsible for chocolate's physiological craving, and ingredients that work positively and synergistically with the nutritional or medical compounds. In other words, in the chocolate product of this invention, ingredients identified as being responsible for chocolate's physiological craving are increased relative to other ingredients in chocolate. In addition, ingredients that are considered harmful are removed or reduced.

As stated above, for the satiation of craving to be strong enough to assure that chocolate will work as a nutritional or medical delivery system, the following ingredients responsible for craving must be present within at least the following ranges:

(A) from about 0.5 to about 200 milligrams, more preferably from about 5 to about 20 milligrams, of one or more biogenic amines per 1 gram of the chocolate product;

(B) from about 10 to about 500 milligrams, more preferably from about 20 to about 200 milligrams, and one or more amino acids per 1 gram of the chocolate product;

In another embodiment, the present invention concerns a improved chocolate-based composition for a delivery system to animals, which comprises:

chocolate;

at least 0.5 milligrams per gram of chocolate of one or more biogenic amines;

at least 10 milligrams per gram of chocolate of one or more amino acids;

at least 1 microgram per gram of chocolate of one or more cannabinoid-like fatty acids;

at least 0.2 milligrams per gram of chocolate of at least one trace mineral; and at least 0.6 milligrams per gram of chocolate of one or more methylxanthine alkaloids.

(C) from about 1 microgram to about 20 milligrams, more preferably from about 10 micrograms to about 10 milligrams, of one or more of: methyl tetrahydroisoquinoline, N-acylethanolamines, and/or anandamide and/or salsolinol per 1 gram of the chocolate product;

(D) from about 0.2 to about 30 milligrams of at least one trace mineral per 1 gram of the chocolate product; and (E) from 0.6 to about 500 milligrams, more preferably from about 35 to about 100 milligrams, of one or more methylxanthine alkaloids per 1 gram of the chocolate product.

The chocolate product of this invention also preferably contains from about 1 to about 5 micrograms of hordenine per 1 gram of chocolate product.

The chocolate product of this invention also preferably contains effective amounts of at least one chocolate aroma and at least one vanilla aroma.

In the present invention, the preferred biogenic amines are tyramine, tryptamine, phenylethylamine, synephrine, serotonin, N-methyl tyramine and octopamine.

The preferred cannabinoid-like fatty acid is selected from the group consisting of N-acylethanolamine, anandamide, and salsolinol.

The preferred methylxanthine alkaloids are caffeine, theophylline and theobromine.

The preferred N-acylethanolamines used in the present invention are N-oleoylethanolamine, N-linolethanolamine, and anandamide (N-arachidonoylethanolamine).

The preferred trace minerals for use in the present invention are magnesium, copper, iron and chromium.

In one preferred embodiment, the novel chocolate product of this invention is composed of a specially formulated, novel chocolate extract containing components (A)–(E). The novel chocolate extract is preferably prepared by a method involving: extracting cocoa raw material (preferably fermented, partially defatted, non-roasted or minimally roasted cocoa cake or low fat (7–15%) chocolate powder (bitter sweet)) with a hydroalcoholic solution in a reactor vessel at a pressure of preferably about 0.62 atmospheres and a temperature of preferably 40°–70° C., more preferably about 50° C.) for about 2 to about 3 hours; storing the resulting extract at low temperatures (preferably 5° C. or less) for a period of preferably 36–144 hours; de-fatting the extract; subjecting the extract to a series of filtration processes that may include centrifugation, filtration, ultra-filtration or cross-flow filtration, and/or pressing through a hydraulic press to remove insoluble (undissolved) particles; pasteurizing the extract; subjecting the extract to ultra-filtration or cross-flow filtration and/or adsorption through ion-exchange resins to further reduce insoluble (undissolved) parts and to optimize the ratio of desired compounds; concentrating the extract under vacuum and low temperatures (preferably 45°–70° C.); refrigerating the extract for a period of preferably about 36–96 hours; and then subjecting the extract to a final fat decantation, separation and removal process. The concentrated, defatted and pasteurized extract may then undergo further fractionation and optimization through adsorption techniques in specialized columns using specific ion exchange resins. Preferably, the extract is first pumped through columns which absorb tannin and phenolic fractions. The extract is then preferably pH-stabilized into an aqueous solution and then pumped through a second set of columns to adsorb the amine, amino acid and methylxanthine alkaloid fractions.

Alternatively, in the chocolate product of the present invention, one or more of components (A)–(E) may be obtained from natural sources other than chocolate.

In addition to endogenous craving-enhancing ingredients (A)–(E), the chocolate product of this invention may further contain one or more exogenously added ingredients which synergistically act with ingredients (A)–(E) to increase the craving properties of the chocolate product composition and/or the efficacy of the chocolate product to treat specific indications. The exogenously added ingredient(s) is preferably selected from the group consisting of dong quai, damiana, jaborandi, capsicum, echinacea, astragalus, evening primrose, feverfew, garlic, ginger, ginkgo, ginseng (panax and siberian), goldenseal, green tea, hawthorn, horse chestnut, kava, licorice, milk thistle, reishi, saw palmetto, St. John's Wort, valerian, vitex, murapuama, catuaba, clavo huasca, sangre de drago, jatoba, yerba mate, acerola, amor seco, avena sativa, boldo, maca, kola nut, bitter orange extract, Garcinia cambogia, ephedrine, chromium, 5-HTP, yohimbe, nettle, bilberry, rhodiola, gotu kola, and suma.

The present invention further provides pharmaceutical compositions comprising: (I) an effective amount of one or more nutrients and/or one or more medicaments and (II) the novel chocolate product of this invention as a carrier for component (I).

A third aspect of the present invention is directed to a method for orally (or otherwise) administering one or more nutrients and/or one or more medicaments to an animal, preferably a human, using the chocolate product of this invention. The method of this invention involves the steps of: (1) providing the pharmaceutical composition of this invention, and (2) orally (or otherwise) administering the pharmaceutical composition to the animal in a therapeutically effective amount for a therapeutically effective period of time.

DETAILED DESCRIPTION OF THE INVENTION

As stated above, a first aspect of the present invention is directed to a specially formulated chocolate product for delivering nutrients and/or medicaments to an animal, preferably a human. The chocolate product of the present invention contains:

(A) from about 0.5 to about 200 milligrams, more preferably from about 5 to about 20 milligrams, of one or more biogenic amines per 1 gram of the chocolate product;

(B) from about 10 to about 500 milligrams, more preferably form about 20 to about 200 milligrams, of one or more amino acids per 1 gram of the chocolate product;

(C) from about 1 microgram to about 20 milligrams, more preferably from about 10 micrograms to about 10 milligrams, of one or more of: methyl tetrahydroisoquinoline, N-acylethanolamines, and/or anandamide and/or salsolinol per 1 gram of the chocolate product;

(D) from about 0.2 to about 30 milligrams of at least one trace mineral per 1 gram of the chocolate product; and (E) from 0.6 to about 500 milligrams, more preferably from about 35 to about 100 milligrams, of one or more methylxanthine alkaloids per 1 gram of the chocolate product.

Non-limiting examples of suitable biogenic amines for use in the chocolate product of this invention are tyramine, N-methyl tyramine, tryptamine, phenylethylamine, phenylethanolamine, serotonin, octopamine, normetanephrine, synephrine, ethylamine, isobutylamine, methylamine, dimethylamine, trimethylamine and isoamylamine. The most preferred biogenic amines for use in the chocolate product of this invention are tyramine, tryptamine, phenylethylamine, serotonin, synephrine, N-methyl tyramine and octopamine.

In a particularly preferred embodiment, the chocolate product of this invention will comprise, as the biogenic amine component:

(a) from about 0.05 to about 30 micrograms of tyramine per 1 gram of the chocolate product;

(b) from about 0.1 to about 20 micrograms of tryptamine per 1 gram of the chocolate product;

(c) from about 0.5 to about 500 micrograms of phenylethylamine per 1 gram of the chocolate product;

(d) from about 0.1 to about 40 micrograms of serotonin per 1 gram of the chocolate product;

(e) from about 0.3 to about 10 milligrams of synephrine per 1 gram of the chocolate product;

(f) from about 1 to about 500 micrograms of N-methyl tyramine per 1 gram of the chocolate product; and (g) from about 1 to about 100 micrograms of octapamine per 1 gram of the chocolate product.

Non-limiting examples of suitable amino acids for use in the chocolate product of this invention are tryptophan, aspartic acid, glutamic acid, methionine, isoleucine, leucine, tyrosine, phenylalanine, lysine and arginine.

Preferably, the amino acid component used in the present invention will contain:

(a) from about 0.5 to about 15 milligrams of tryptophan per 1 gram of the chocolate product;

(b) from about 0.5 to about 15 milligrams of phenylalanine per 1 gram of the chocolate product;

(c) from about 1 to about 15 milligrams of arginine per 1 gram of the chocolate product;

(d) from about 0.5 to about 15 milligrams of tyrosine per 1 gram of the chocolate product;

(e) from about 3 to about 50 milligrams of aspartic acid per 1 gram of the chocolate product;

(f) from about 3 to about 50 milligrams of glutamic acid per 1 gram of the chocolate product;

(g) from about 0.5 to about 10 milligrams of methionine per 1 gram of the chocolate product;

(h) from about 1 to about 20 milligrams of isoleucine per 1 gram of the chocolate product;

(i) from about 1 to about 20 milligrams of leucine per 1 gram of the chocolate product; and (j) from about 1 to about 10 milligrams of lysine per 1 gram of the chocolate product.

The preferred N-acylethanolamines used in the present invention are N-oleoylethanolamine, N-linolethanolamine, and anandamide (N-arachidonoylethanolamine).

The preferred trace minerals for use in the present invention are magnesium, copper, iron and chromium. Preferably, the trace mineral component of this invention will contain from about 0.1 to about 10 milligrams of magnesium per 1 gram of chocolate product, from about 0.01 to about 5 milligrams of copper per 1 gram of chocolate product, and from about 0.01 to about 5 milligrams of iron per 1 gram of chocolate product.

The most preferred methylxanthine alkaloids for use in the present invention are theobromine, caffeine and theophylline.

Preferably, the methylxanthine alkaloid component used in the present invention contains from about 5 to about 100 milligrams of theobromine per 1 gram of the chocolate product, from about 1 to about 50 milligrams of caffeine per 1 gram of the chocolate product, and from about 0.1 to about 20 milligrams of theophylline per 1 gram of the chocolate product. More preferably, the methylxanthine alkaloid component used in the present invention contains from about 30 to about 60 milligrams of theobromine per 1 gram of the chocolate product, from about 5 to about 30 milligrams of caffeine per 1 gram of the chocolate product, and from about 0.5 to about 5 milligrams of theophylline per 1 gram of the chocolate product.

The chocolate product of this invention also preferably contains from about 5 to about 40 micrograms of salsolinol per 1 gram of chocolate product and from about 1 to about 5 micrograms of hordenine per 1 gram of chocolate product.

The chocolate product of this invention also preferably contains effective amounts of at least one chocolate aroma and at least one vanilla aroma.

In addition, the chocolate product of this invention may contain from 0 to about 80 milligrams of fat per 1 gram of the chocolate product.

In the chocolate product of this invention, the achievement of the enhanced concentration levels of the ingredients responsible for craving (i.e., components (A)–(E)) can be achieved by an unusual manufacturing process, the details of which are described below.

The preferred starting material (i.e., raw material) for use in making the chocolate product of this invention is fermented, partially defatted, non-roasted or minimally roasted cocoa cake or low fat (7–15%) chocolate powder (bitter sweet). The cocoa may be roasted, but roasting affects the profile of the marker compounds which are desired in the product of this invention and, therefore, is not preferred. The cocoa starting material may be Dutch processed (alkalinized). The preferred cocoa raw material, with the preferred content of desired compounds, is found in Brazil, from the states of Bahia and Para. Other preferred sources of the cocoa raw material which can be used in making the chocolate product of this invention include Ghana, New Guinea and Malaysia.

The cocoa starting material (either cake or powder) is loaded into reactor vessels (e.g., steam-jacketed 16.000 liter vessels) operating at preferred pressures of 0.6 to 2.0 atmospheres (more preferably 0.7 to 1.1 atmospheres) with controlled vapor. The cocoa is extracted under intense agitation and warm or moderate heat (preferably between about 40° C. and 70° C.) for 2 to 3 hours. The reactor vessels have chillers (i.e., cold water condensers) attached to them for the condensation and recovery of solvent and solvent vapors (ethanol) emitted during the process of extraction. The process is known as a closed circuit temperature and pressure controlled extraction or "dynamic maceration". Extraction is performed with a hydroalcoholic solution. The hydroalcoholic solution is preferably a 50/50 blend of water and sugar cane ethanol but the ratio of water to ethanol may vary considerably. The pH of the hydroalcoholic solution may be modified to optimize extraction of desirable compounds. A ratio of 5 to 15 parts (more preferably 6 to 10 parts) by volume (liters) of hydroalcoholic solution for every 1 part of cocoa raw material by weight (kilograms) is preferably used in the extraction process.

The resulting extract is stored in a refrigerated room (preferably 5° C. or less) for 36 to 144 hours, more preferably about 48 to 96 hours. The fat is decanted, separated and removed from the extract every 12 or so hours. The partially de-fatted extract is then stored again under refrigeration (preferably 5° C. or less) for another 12 to 120 hours (more preferably 48 to 96 hours), after which residual fat is decanted and removed for a second time. The de-fatting process constitutes removing the supernatant (fat) from the extract every 12 hours or so until fat has been removed to an ideal level preferably less than 7%, more preferably less than 3%, most preferably 1%, of total).

The extract then undergoes a series of filtration processes that may include centrifugation (preferably using a basket centrifuge with a capacity of 1000 kilograms of extracted cocoa paste) for preferably 1–3 hours; filtration (preferably using a Sparkle filtering system manufactured by Niro, with a capacity of 2500 liters per hour of cocoa solution); ultra-filtration or cross-flow filtration (preferably using Koch Membranes Ultra Filtration System with sintered membranes at 10,000 to 25,000 daltons mesh size and capacity of 20,000 liters flow through per unit per day), or pressing through a hydraulic press to remove insoluble (undissolved) particles. The residual cake is then washed to recover additional solvent.

The extract is then pasteurized (preferably using a Plate Pasteurizer, manufactured by Inoxil Brazil), with a capacity of 1800 liters per hour) at moderate temperatures (preferably 80°110° C., more preferably about 90° C.) for 40–60 seconds (more preferably 45 seconds) and cooled (chilled) with cold water (preferred temperature being between 15 and 25° C., more preferably about 22° C.) to reduce the microbial load while minimizing the effect on desired compounds.

The extract may then undergo ultra-filtration or cross-flow filtration and/or adsorption through ion-exchange resins to further reduce insoluble (undissolved) parts and to optimize the ratio of desired compounds.

The extract is then concentrated under vacuum (preferably using a Multi-Stage Falling Film Evaporator, operating at 3 stages, manufactured by GEA, and with a capacity of 5000 liters per hour) at low temperatures (preferably 45°70° C., more preferably 60° C.).

The extract is then refrigerated a third time for preferably 36 to 96 hours (more preferably about 48 hours), and a final fat decantation, separation and removal process is undertaken.

Other ingredients may be added to the extract at this point and blended for preparation to drying.

Depending on the added ingredients, an excipient (e.g., up to 25% maltodextrin (CPC type 1920) or other suitable excipient) may be added to the extract blend. The mixture is blended and spray dried at temperatures of preferably from about 180° C. to about 200° C. (more preferably 190° C.) (inlet) and from about 80° C. to about 100° C. (more preferably about 90° C.) (outlet). The extract may also be vacuum dried, tray dried, or freeze dried.

The powdered extract is then packed in double poly lined bags and placed, with a dessicant, into fiber drums.

The concentrated, defatted and pasteurized extract may undergo further fractionation and optimization through adsorption techniques in specialized columns utilizing specific ion exchange resins. These further purification processes are accomplished by pumping the concentrated, defatted, and filtered extract through specially designed columns packed with ion exchange resins that have specific affinity to key components within the extract. The extract is first pumped through columns packed with ion exchange resins (e.g., Mitsubishi Chemical Diaion Exchange Resins HP20 or HP21 or SP825 or SP850) to adsorb the tannin and phenolic fractions. The resins are washed (desorbed) with ethanol to remove the tannin and phenolic fraction. The extract is then pH-modified or stabilized into an aqueous solution. The pH-regulated aqueous solution of slurry is pumped through a second set of columns packed with ion exchange resins (e.g., Dow Chemicals DowEx-50 or Mitsubishi Chemicals Diaion WK 100 or WT 01S resins) to adsorb the amine, amino acid and methylxanthine fractions. The resins are washed (desorbed) with an acidic ethanol solution (preferably 50–95%) to remove the amine and amino acid fractions.

The two ensuing separated fractions consist of an enriched tannin or phenolic extract and an amine, amino acid and methylxanthine extract.

The chocolate product of this invention preferably does not include the tannin/phenolic extract, sugar or fat.

In one embodiment of the chocolate product of the present invention, one or more of the components (A)–(E) may be obtained from natural sources other than chocolate.

Table I below lists natural, non-chocolate sources of the ingredients used in the chocolate product of this invention.

TABLE I

| Ingredient | Natural Source |
|---|---|
| Biogenic amines | pineapple, tomato, banana orange |
| N-acylethanolamines | wine, cheese, beer, |
| Magnesium | pickled herring |
| Methylxanthines | coffee, guarana |
| Chocolate aroma | chocolate beans, chocolate fruit |
| Vanilla aroma | vanilla beans |

In addition to endogenous craving-enhancing ingredients (A)–(E), the chocolate product of this invention may further contain one or more exogenously added ingredients which synergistically act with ingredients (A)–(E) to increase the craving properties of the chocolate product composition and/or the efficacy of the chocolate product to treat specific indications. The exogenously added ingredient(s) is preferably selected from the group consisting of dong quai, damiana, jaborandi, capsicum, echinacea, astragalus, evening primrose, feverfew, garlic, ginger, ginkgo, ginseng panax and siberian), goldenseal, green tea, hawthorn, horse chestnut, kava, licorice, milk thistle, reishi, saw palmetto, St. John's Wort, valerian, vitex, murapuama, catuaba, clavo huasca, sangre de drago, jatoba, yerba mate, acerola, amor seco, avena sativa, boldo, maca, kola nut, bitter orange extract, Garcinia cambogia, ephedrine, chromium, 5-HTP, yohimbe, nettle, bilberry, rhodiola, gotu kola, and suma.

The addition of the exogenous ingredients can provide the chocolate product composition with additional nutritional benefits. Set forth below are various formulations of the chocolate product composition listing at least some of the endogenous and exogenous ingredients responsible for the indicated therapeutic benefits.

---

DIET (WEIGHT LOSS)

Thermogenic and Appetite Suppressant

Endogenous

Theobromine
Caffeine
Theophylline
Synephrine

Exogenous*

Guarana
Green-Tea
Jaborandi
Capsicum
Yerba Mate
Kola Nut
Bitter Orange extract
Ephedrine
Garcinia cambogia
Chromium

Stimulant

Endogenous

Caffeine
Theobromine
Theophylline

Exogenous*:

Guarana
Jaborandi
Yerba mate
Kola Nut
Capsicum
Ephedrine
Green-Tea
Ginseng (Panax and Siberian)

Enzyme (Phosphodiesterase) inhibition

Endogenous

Theobromine
Caffeine
Theophylline
Synephrine

DIET (WEIGHT LOSS) -continued

Exogenous*:

Alstonia scholaris
*Amomum* species
Aralia cordata
Areca catechu
*Asiasarum* spp.
Bupleurum falcatum
Caesalpinia sappan
*Cassia* spp.
Coptis teeta
Daphne genkwa
Eucalyptus robusta
Forsythia suspensa
Ginkgo biloba
Glycyrrhiza glabra
Lonicera japonica
Paeonia rubra
Panax ginseng
Perilla frutescens
Pilocarpus microphyllus or P. jaborandi
Salvia miltiorrhiza
Synephrine
Ephedrine
Bitter Orange extract
Guarana
Yerba mate
Kola Nut
Green-Tea

Appetite Suppressant through satiation of cravings

Endogenous

Biogenic Amines:
Tyramine
Phenylethylamine
Tryptamine
Serotonin
Methyl tetrahydroisoquinoline, N-acylethanolamines and/or anandamide and/or salsolinol
Magnesium, Copper & Iron
Chocolate and Vanilla Aromas Exogenous*:

Magnesium
Vanilla extract
Chocolate bean and fruit extract

*These may be added in amounts of 10–2000 mg/g in the form of an extract, or 2–20 g in the form of dried herb.

---

SEXUAL FUNCTION (APHRODISIAC)/

Increase of mood altering neurochemicals

Endogenous

Biogenic Amines:
Tyramine
Phenylethylamine
Tryptamine
Serotonin
Methyl tetrahydroisoquinoline, N-acylethanolamines and/or anandamide and/or salsolinol Chocolate and Vanilla Aromas Exogenous*

Marapuama
Guarana
Catuaba
Maca
Yohimbe
Vanilla Extract/Aroma
Kava

-continued

Local Vasodilator

Endogenous

Synephrine
Exogenous*:

Ginkgo
Bilberry
Ephedrine

Thermogenic and Stimulant

Endogenous

Theobromine
Caffeine
Theophylline
Synephrine
Exogenous*

Guarana
Green-Tea
Jaborandi
Capsicum
Yerba Mate
Kola Nut
Bitter Orange extract
Ephedrine
Garcinia cambogia
Chromium

WOMAN'S HEALTH

Mitigate the increased needs for mineral supplementation

Endogenous

Magnesium
Iron
Copper
Exogenous*

Magnesium
Iron
Copper

Increase of mood altering neurochemicals

Endogenous

Biogenic Amines:
Tyramine
Phenylethylamine
Tryptamine
Serotonin
Methyl tetrahydroisoquinoline, N-acylethanolamines and/or anandamide and/or salsolinol Chocolate and Vanilla Aromas
Exogenous*

Guarana
Maca
Vanilla Extract/Aroma
Kava
Valerian
St. John's Wort

Diuretic

Endogenous

Caffeine
Theobromine
Theophylline
Exogenous*

Guarana
Yerba mate
Kola Nut
Green-Tea
Nettle

-continued

COLD AND FLU SYMPTOMS

Thermogenic

Endogenous

Theobromine
Caffeine
Theophylline
Synephrine
Exogenous*

Guarana
Green-Tea
Jaborandi
Capsicum
Yerba Mate
Kola Nut
Bitter Orange extract
Ephedrine
Garcinia cambogia
Chromium

Bronchioldialtor

Endogenous

Synephrine
Non-endogenous*

Synephrine
Ephedrine
Jaborandi
Ma Huang

COGNITIVE FUNCTION

Increase of mood altering neurochemicals

Endogenous

Biogenic Amines:
Tyramine
Phenylethylamine
Tryptamine
Serotonin
Methyl tetrahydroisoquinoline, N-acylethanolamines and/or anandamide and/or salsolinol
Chocolate and Vanilla Aromas
Exogenous*

Kava
Valerian
St. John's Wort

Anti-Depressant (Hysteroid Dysphoria)

Endogenous

Phenylethylamine
Exogenous*

St. John's Wort
5-HTP
Rhodiola

*These may be added in amounts of 10–2000 mg/g in the form of an extract or purified compound, or 2–20 g in the form of dried herb.

A second aspect of the present invention is directed to a pharmaceutical composition containing: (I) one or more nutrients and/or one or more medicaments, and (II) the chocolate product of this invention as a carrier for component (I).

The chocolate product can be used in the composition in an amount carriers are conventionally used in pharmaceutical compositions.

Non-limiting examples of pharmaceutical compositions within the scope of the present invention include thermogenic and appetite suppressants; stimulants; enzyme phosphodiesterase) inhibitors; aphrodisiacs; vasodilators; diuretics; cold and flu medications; bronchodilators; and anti-depressants.

A third aspect of the present invention is directed to a method for orally administering one or more nutrients and/or one or more medicaments to an animal, preferably a human, involving the steps of: (1) providing the pharmaceutical composition of this invention, and (2) orally (or other wise) administering the composition to the animal in a therapeutically effective amount for a therapeutically effective period of time.

The terms "effective amount" and "effective period of time" with respect to the amount and duration of administration of the pharmaceutical composition is that amount and time period which is sufficient to promote the particular therapeutic benefits provided by the composition. Persons of ordinary skill in the art can easily determine optimum dosages, dosing methodologies, and repetition rates.

The skilled artisan will be aware that a variety of exemplary embodiments of the present invention have been described above in enabling detail, and the embodiments are truly examples of a larger set that all fall within the spirit and scope of the present invention. Many changes may be made in these embodiments without departing from that spirit and scope. For at least this reason the claims below should be given their broadest interpretation in light of the disclosure.

What is claimed is:

1. A chocolate-based product for a delivery system for nutrients, medications, or combinations thereof, to humans, which product comprising:
   defatted chocolate extract;
   one or more biogenic amines added to the product to obtain a composition of at least 0.5 milligrams per gram of product;
   one or more amino acids added to the product to obtain a composition of at least 10 milligrams per gram of product;
   one or more fatty acids; having cannabinoid chemical properties added to product to obtain a composition of at least 1 milligram per gram of product;
   at least one trace mineral; added to the product to obtain a composition of at least 0.2 milligrams per gram of product; and
   one or more methylxanthine alkaloids added to the product to obtain a composition of at least 0.6 milligrams per gram of product.

2. The chocolate-based product of claim 1 wherein the biogenic amines are present in a range of from 5 to 20 milligrams per gram of product.

3. The chocolate-based product of claim 1 wherein the amino acids occur in a range of from 20 to 200 milligrams per gram of product.

4. The chocolate-based product of claim 1 wherein said fatty acids having cannabinoid chemical properties are selected from the group consisting of methyl tetrahydroisoquinoline, N-acylethanolamines, anandamide, salsolinol or combinations thereof are present in a range of from about 10 micrograms to 10 milligrams per gram of product.

5. The chocolate-based product of claim 1 wherein said trace mineral or minerals occur in a range of from 0.2 to 30 milligrams per gram of product.

6. The chocolate-based product of claim 1 wherein the one or more methylxanthine alkaloids occur in a range of from 35 to 100 milligrams per gram of product.

7. The chocolate-based product of claim 1 further comprising from 1 to 5 micrograms of hordenine per gram of product.

8. The chocolate-based product of claim 1 which further comprising chocolate aroma, a vanilla aroma or combinations thereof.

9. The chocolate-based product of claim 1 wherein the biogenic amines are selected from the group consisting of tyramine, tryptamine, phenylethylamine, synephrine, serotonin, N-methyl tyramine, octopamine and combinations thereof.

10. The chocolate-based product of claim 1 wherein the fatty acid having cannabinoid chemical properties is selected from the group consisting of N-acylethanolamines, anandamide, salsolinol and combinations thereof.

11. The chocolate-based product of claim 1 wherein the methylxanthine alkaloids are selected from the group of caffeine, theophylline, theobromine, and combinations thereof.

12. A chocolate-based product for a delivery system for nutrients, medications, or combinations thereof, to humans, which product comprises:
   defatted chocolate extract;
   one or more biogenic amines added to the product to obtain a composition of at least 0.5 milligrams per gram of product;
   one or more amino acids added to the product to obtain a composition of at least 10 milligrams per gram of product;
   one or more fatty acids having cannabinoid chemical properties added to the product to obtain a composition of at least 1 microgram per gram of product;
   at least one trace mineral added to the product to obtain a composition of at least 0.2 milligrams per gram of product; and
   one or more methylxanthine alkaloids added to the product to obtain a composition of at least 0.6 milligrams per gram of product;
   wherein the biogenic amines are selected from the group consisting of tyramine, trptamine, phenylethylamine, synephrine, serotonin, N-methyl tyramine, octapamine and combinations thereof;
   wherein the fatty acid having cannabinoid chemical properties is an N-acylethanolamine selected from the, group consisting of N-oleoylerthanolamine, -lonolethanolamine, N-arachidonoylethanolamine and combinations thereof;
   wherein the trace mineral or minerals are selected from the group consisting of magnesium, iron, copper, and chromium; and
   wherein the methylxanthine alkaloids are selected from the group consisting of caffeine, theophylline, theobromine and combinations thereof.

13. A chocolate-based product for a delivery system for nutrients, medications, or combinations thereof, to humans, which product comprises;
   defatted chocolate extract;
   one or more biogenic amines added to the product to obtain a composition of at least 0.5 milligrams per gram of product;
   one or more amino acids added to the product to obtain a composition of at least 10 milligrams per gram of product;
   one or more fatty acids having cannabinoid chemical properties added to the product to obtain a composition of at least 1 microgram per gram of product;

at least one trace mineral added to the product to obtain a composition of at least 0.2 milligrams per gram of product; and one or more methylxanthine alkaloids added to the product to obtain a composition of at least 0.6 milligrams per gram of product;

wherein the biogenic amines are selected from the group consisting of tyramine, trptamine, phenylethylamine, synephrine, serotonin, N-methyl tyramine, octapamine and combinations thereof present in a concentration of about 5 mg to 20 milligrams per gram of chocolate product;

wherein the fatty acid having cannabinoid chemical properties is selected from the group consisting of acylethanolamines, anandamide, salsolinol and combinations thereof present in a concentration of about 10 micrograms to 10 milligrams per gram of chocolate product;

wherein the trace mineral or minerals are selected from the group consisting of magnesium, iron, copper, chromium and combinations thereof in a concentration of about 0.2 to 30 milligrams per gram of chocolate product; and wherein the methylxanthine alkaloids are selected from the group consisting of caffeine, theophylline, theobromine and combinations thereof in a concentration of about 35 to 100 milligrams per gram of product.

14. A method for preparing a chocolate-based product for a delivery system to humans, comprising the steps of:
(a) extracting a chocolate material from cocoa raw material in a manner to provide a defatted chocolate extract;
(b) subjecting the resulting defatted chocolate extract to one or more processes to optimize the ratio of desired compounds to product content, wherein the desired compounds and ratios are:
at least 0.5 milligrams per gram of product of one or more biogenic amines,
at least 10 milligrams per gram of product of one or more amino acids,
at least 1 microgram per gram of product of one or more fatty acids having cannabinoid chemical properties,
at least 0.2 milligrams per gram of product of at least one trace mineral, and
at least 0.6 milligrams per gram of product of one or more methylxanthine alkaloids.

15. The method of claim 14 wherein the processes result in the biogenic amines being present in a range of from about 5 to 20 milligrams per gram of chocolate product.

16. The method of claim 14 wherein the processes result in the amino acids being present in a range of from 20 to 200 milligrams per gram of chocolate product.

17. The method of claim 14 wherein the processes result in methyl tetrahydroisoquinoline, N-acylethanolamines, anandamide, salsolinol and combinations thereof being present in a range of from about 10 micrograms to 10 milligrams per gram of chocolate product.

18. The method of claim 14 wherein the processes result in the trace mineral or minerals being present in a range of from 0.2 to 30 milligrams per gram of chocolate product.

19. The method of claim 14 wherein the processes result in the one or more methylxanthine alkaloids being present in a range of from about 35 to 100 milligrams per gram of chocolate product.

20. The method of claim 14 wherein the biogenic amines are present and include components selected from the group consisting of tyramine, trptamine, phenylethylamine, synephrine, serotonin, methyl tyramine, octapamine and combinations thereof.

21. The method of claim 14 wherein the processes result in the fatty acid having cannabinoid chemical properties being present and selected from the group consisting of N-acylethanolamines, anandamide, salsolinol and combinations thereof.

22. The method of claim 14 wherein the processes result in the methylxanthine alkaloids being present and selected from the group consisting of caffeine, theophylline, theobromine and combinations thereof.

23. The method of claim 10 wherein the processes result in the fatty acid having cannabinoid chemical properties being an N-acylethanolamine selected from the group consisting of N-oleoylethanolamine, monolethanolamine, N-arachidonoylethanolamine and combinations thereof.

24. The method of claim 14 wherein the processes result in the trace mineral or minerals being selected from of the group consisting of magnesium, iron, copper, chromium and combinations thereof.

25. The method of claim 14 comprising an additional step for adding further desirable materials to the chocolate product;
wherein said chocolate product does not include sugar, fat or combinations thereof.

26. The method of claim 25 wherein the added desirable material is from about 1 to 5 micrograms of hordenine per gram of chocolate product.

27. The method of claim 25 wherein the added desirable material is selected from the group consisting of a chocolate aroma, a vanilla aroma and combinations thereof.

28. The method of claim 25 wherein one or more ingredients are added to react synergistically with the desired compounds listed in step (b).

29. The method of claim 28 wherein said ingredients added are selected from the group consisting of dong quai, damiana, jaborandi, capsicum, iberian, astragalus, evening primrose, feverfew, garlic, ginger, ginko, ginsing, either panax or iberian, goldenseal, green tea, hawthorn, horse chestnut, kava, licorice, milk thistle, reishi, saw palmetto, St. John's wort, valerian, vitex, murapuama, ctuaba, clavo huasca, sangre de drago, jatoba, yerbe mate, acerola, amor seco, avena sativa, boldo, maca, kola nut, bitter orange extraxt, Garcinia cambogia, ephedrine, chromium, 5-HTP, yohimbe, nettle, bilberry, rhodiola, gotu, kola, suma and combinations thererof.

30. The chocolate-based product of claim 1 further comprising components selected from the group consisting of dong quai, damiana, jaborandi, capsicum, echinacea, astragalus, evening primrose, feverfew, garlic, ginger, ginko, ginsing, either panax or siberian, goldenseal, green tea, hawthorn, horse chestnut, kava, licorice, milk thistle, reishi, saw palmetto, St. John's wort, valerian, vitex, murapuama, ctuaba, clavo huasca, sangre de drago, jatoba, yerbe mate, acerola, amor seco, avena sativa, boldo, maca, kola nut, bitter orange extraxt, Garcinia cambogia, ephedrine, chromium, 5-HTP, yohimbe, nettle, bilberry, rhodiola, gotu, kola, suma and combinations thereof.

31. The chocolate-based product of claim 1 further comprising an added nutrient for which the chocolate-based product is then a delivery vehicle.

32. The chocolate-based product of claim 1 further comprising an added medicinal composition for which the chocolate-based product is then a delivery vehicle.

33. The method of claim 25 further comprising a step for adding a nutrient for which the chocolate-based product is then a delivery vehicle.

34. The method of claim 25 further comprising a step for adding a medicinal composition for which the chocolate-based product is then a delivery vehicle.

35. The chocolate-based product of claim 12 further comprising components selected from the group consisting of dong quai, damiana, jaborandi, capsicum, echinacea, astragalus, evening primrose, feverfew, garlic, ginger, ginko, ginsing, either panax or siberian, goldenseal, green tea, hawthorn, horse chestnut, kava, licorice, milk thistle, reishi, saw palmetto, St. John's wort, valerian, vitex, murapuama, ctuaba, clavo huasca, sangre de drago, jatoba, yerbe mate, acerola, amor seco, avena sativa, boldo, maca, kola nut, bitter orange extraxt, Garcinia cambogia, ephedrine, chromium, 5-HTP, yohimbe, nettle, bilberry, rhodiola, gotu, kola, suma and combinations thereof.

36. The chocolate-based product of claim 13 further comprising components selected from the group consisting of dong quai, damiana, jaborandi, capsicum, echinacea, astragalus, evening primrose, feverfew, garlic, ginger, ginko, ginsing, either panax or siberian, goldenseal, green tea, hawthorn, horse chestnut, kava, licorice, milk thistle, reishi, saw palmetto, St. John's wort, valerian, vitex, murapuama, ctuaba, clavo huasca, sangre de drago, jatoba, yerbe mate, acerola, amor seco, avena sativa, boldo, maca, kola nut, bitter orange extraxt, Garcinia cambogia, ephedrine, chromium, 5-HTP, yohimbe, nettle, bilberry, rhodiola, gotu, kola, suma and combinations thereof.

37. A chocolate-based product for a delivery system for nutrients, medications, or combinations thereof, to humans, which product comprises;
   defatted chocolate extract;
   one or more biogenic amines added to the product to obtain a composition of between about 5 to 20 milligrams per gram of product;
   one or more amino acids added to the product to obtain a composition of between about 10 micrograms to 10 milligrams per gram of product;
   one or more fatty acid having cannabinoid chemical properties added to the product to obtain a composition of between about 10 micrograms to 10 milligrams per gram of product;
   at least one trace mineral added to the product to obtain a composition of between about 0.2 to 30 milligrams per gram of product; and
   one or more methylxanthine alkaloids added to the product to obtain a composition of between about 35 to 100 milligrams per gram of product;
   wherein the one or more biogenic amines are selected from the group consisting of tyramine, trptamine, phenylethylamine, synephrine, serotonin, N-methyl tyramine, octapamine and combinations thereof;
   wherein the one or more amino acids are selected from the group consisting of tryptophan, phenylalanine, arginine, tyrosine, aspartic acid, glutamic acid, methionine, isoleucine, leucine, lysine and combinations thereof;
   wherein the one or more fatty acid having cannabinoid chemical properties are selected from the group consisting of acylethanolamines, anandamide, salsolinol and combinations thereof;
   wherein the one or more trace mineral or minerals are selected from the group consisting of magnesium, iron, copper, chromium and combinations thereof; and
   wherein the one or more methylxanthine alkaloids are selected from the group consisting of caffeine, theophylline, theobromine and combinations thereof.

38. A chocolate-based product for a delivery system for nutrients, medications, or combinations thereof, to humans, which product consists essentially of;
   defatted chocolate extract;
   one or more biogenic amines added to the product to a composition of between about 5 to 20 milligrams per gram of product;
   one or more amino acids added to the product to a composition of between about 10 micrograms to 10 milligrams per gram of product;
   one or more fatty acid having cannabinoid chemical properties added to the product to a composition of between about 10 micrograms to 10 milligrams per gram of product;
   at least one trace mineral added to the product to a composition of between about 0.2 to 30 milligrams per gram of product; and
   one or more methylxanthine alkaloids added to the product to a composition of between about 35 to 100 milligrams per gram of product;
   wherein the one or more biogenic amines are selected from the group consisting of tyramine, trptamine, phenylethylamine, synephrine, serotonin, N-methyl tyramine, octapamine and combinations thereof
   wherein the one or more amino acids are selected from the group consisting of tryptophan, phenylalanine, arginine, tyrosine, aspartic acid, glutamic acid, methionine, isoleucine, leucine, lysine and combinations thereof;
   wherein the one or more fatty acid having cannabinoid chemical properties are selected from the group consisting of acylethanolamines, anandamide, salsolinol and combinations thereof;
   wherein the one or more trace mineral or minerals are selected from the group consisting of magnesium, iron, copper, chromium and combinations thereof; and
   wherein the one or more methylxanthine alkaloids are selected from the group consisting of caffeine, theophylline, theobromine and combinations thereof.

* * * * *